United States Patent [19]

Dvorak

[11] 4,395,571

[45] Jul. 26, 1983

[54] PROCESS FOR THE PREPARATION OF D,1-2-(6-METHOXY-2-NAPHTHYL)PROPIONIC ACID

[75] Inventor: Charles A. Dvorak, Palo Alto, Calif.

[73] Assignee: Syntex (U.S.A.) Inc., Palo Alto, Calif.

[21] Appl. No.: 384,445

[22] Filed: Jun. 3, 1982

[51] Int. Cl.³ ............................................ C07C 65/105
[52] U.S. Cl. ................................... 562/466; 568/433; 568/438; 568/440; 562/408
[58] Field of Search ................ 562/466, 408; 568/433, 568/438, 440

[56] References Cited

U.S. PATENT DOCUMENTS

| | | | |
|---|---|---|---|
| 3,652,683 | 3/1972 | Harrison | 562/466 |
| 3,658,858 | 4/1972 | Harrison | 562/466 |
| 3,658,863 | 4/1972 | Harrison | 562/466 |
| 3,663,584 | 5/1972 | Alvarez | 562/466 |
| 3,694,476 | 9/1972 | Alvarez | 562/466 |
| 3,808,277 | 4/1974 | Alvarez | 562/466 |
| 3,821,253 | 6/1974 | Fried et al. | 562/466 |
| 3,868,405 | 2/1975 | Brain et al. | 562/466 |
| 3,891,712 | 6/1975 | Fried et al. | 562/466 |
| 3,896,157 | 7/1975 | Fried et al. | 562/466 |
| 3,906,038 | 9/1975 | Fried et al. | 562/466 |

Primary Examiner—Paul J. Killos
Attorney, Agent, or Firm—Annette M. Moore; Tom M. Moran

[57] ABSTRACT

Racemic mixtures of d,1-2-(6-methoxy-2-naphthyl)-propanal are resolved by forming a condensation product with N-R-D-glucamine or a salt thereof where R is hydrogen, alkyl of 1 to 36 carbon atoms or cycloalkyl of 3 to 8 carbon atoms, from which a product substantially enriched in d-2-(6-methoxy-2-naphthyl)propanal can be obtained and then can be selectively oxidized to d-2-(6-methoxy-2-naphthyl)propionic acid.

17 Claims, No Drawings

PROCESS FOR THE PREPARATION OF D,1-2-(6-METHOXY-2-NAPHTHYL)PROPIONIC ACID

BACKGROUND OF THE INVENTION

This invention relates to a process for preparing d-2-(6-methoxy-2-naphthyl)propionic acid comprising resolving a racemic mixture of the d,1-2-(6-methoxy-2-naphthyl)propanal intermediate to yield a product substantially enriched in d-2-(6-methoxy-2-naphthyl)propanal which is then selectively oxidized to obtain d-2-(6-methoxy-2-naphthyl)propionic acid.

d-2-(6-Methoxy-2-naphthyl)propionic acid is a well-known anti-inflammatory, analgesic and anti-pyretic agent which is described and claimed in U.S. Pat. No. 3,904,682. Processes for the preparation of d-2-(6-methoxy-2-naphthyl)propionic acid are described in U.S. Pat. Nos. 4,246,164; and 4,246,193 and French Pat. No. 2,377,370.

BRIEF SUMMARY OF THE INVENTION

In summary, the process of this invention comprises resolving a racemic mixture of d,1-2-(6-methoxy-2-naphthyl)propanal by forming a condensation product with N-R-D-glucamine or a salt thereof where R is hydrogen, alkyl of 1 to 36 carbon atoms, preferably 1 to 18 carbon atoms, or cycloalkyl of 3 to 8 carbon atoms to yield a product substantially enriched in d-2-(6-methoxy-2-naphthyl)propanal. The resulting d-2-(6-methoxy-2-naphthyl)propanal is then selectively oxidized to d-2-(6-methoxy-2-naphthyl)propionic acid by methods well-known in the art. Racemic mixtures of d,1-2-(6-methoxy-2-naphthyl)propanal which form during known chemical synthesis of the aldehyde, such as the method disclosed in U.S. Pat. No. 3,562,336, are the presently preferred starting material for the resolution method of this invention.

The term "alkyl" as used herein refers to and includes straight and branched chain hydrocarbon groups having 1 to 36 carbon atoms. Typical alkyl groups include methyl, ethyl, n-propyl, i-propyl, n-butyl, i-butyl, n-hexyl, n-octyl, n-dodecyl, n-octadecyl, n-docosanyl, n-hexatricontanyl, and the like.

The term "cycloalkyl" as used herein refers to and includes cycloaliphatic hydrocarbon groups having 3 to 8 carbon atoms. Typical cycloalkyl groups include cyclopropyl, cyclobutyl, cyclopentyl, cyclohexyl, methylcyclohexyl, cycloheptyl and cyclooctyl. Of the cycloalkyl groups, cyclohexyl is presently preferred.

Presently preferred resolving agents within the scope of this invention are the salts of N-R-D-glucamine, particularly N-methyl-D-glucamine, N-n-propyl-D-glucamine, N-n-butyl-D-glucamine, and N-n-octyl-D-glucamine. The N-R-D-glucamines may be prepared by the methods disclosed in U.S. Pat. Nos. 4,246,164 and 4,246,193 which patents are incorporated herein by reference. Suitable glucamine salts include salts of inorganic acids such as hydrochloric acid, sulfuric acid and the like and strong organic acids such as p-toluenesulfonic acid and the like. The salts are prepared by combining stochiometric amounts of the acid and the amine.

The resolution contemplated by this invention is conducted in an inert organic solvent having a pronounced difference between the solubilities of the condensation product of d-2-(6-methoxy-2-naphthyl)propanal with the resolving agent and the condensation product of 1-2-(6-methoxy-2-naphthyl)propanal with the resolving agent, generally at temperatures between room or ambient temperature and an elevated temperature generally up to the reflux temperature of the sovlent utilized. The condensation product of d-2-(6-methoxy-2-naphthyl)propanal with the resolving agent (for example, the salts of N-methyl-D-glucamine, N-n-Propyl-D-glucamine, N-n-butyl-D-glucamine or N-n-octyl-D-glucamine) should be significantly less soluble in the solvent than is the condensation product of 1-2-(6-methoxy-2-naphthyl)propanal with the resolving agent and, accordingly, upon the cooling of a heated solution thereof, generally to or about ambient or room temperature, such condensation product of d-2-(6-methoxy-2-naphthyl)propanal with the resolving agent will be preferentially crystallized therefrom.

Suitable solvents include $C_1$ to $C_{10}$ monohydric alcohols, such as, for example, methanol, ethanol, n-propanol, isopropanol, butanol, pentanol, hexanol, cyclohexanol, 2-ethylhexanol, benzyl alcohol, furfuryl alcohol, and the like, $C_2$ to $C_6$ dihydric alcohols, such as, for example, ethylene glycol, 1,2-propylene glycol, 1,3-propylene glycol, and the like, $C_3$ to $C_4$ trihydric alcohols, such as for example, glycerol, and the like. Other solvents include ethers such as tetrahydrofuran, diethylether, mono- and di(lower)alkyl ether of ethylene glycol and diethylene glycol. Other suitable solvents are dimethylsulfoxide, sulfolanes, formamide, dimethylformamide, N-methyl pyrrolidone, pyridine, dioxane, dimethylacetamide, esters such as ethyl acetate and the like. Hydrocarbon solvents such as aromatic solvent, e.g. toluene, benzene and the like and alkanes such as heptane are particularly useful in the present invention. It is also contemplated that mixtures of the above solvents may be used.

The starting material [i.e., the racemic mixture of d,1-2-(6-methoxy-2-naphthyl)propanal] and the resolving agent in a molar ratio of 1:1 are heated in a solvent to an elevated temperature, generally to a temperature in the range from about 60° C. to about 100° C. or the reflux temperature of the solvent. The salt of N-R-D-glucamine may be preformed as described supra or may be formed in situ. If formed in situ an acid such as an inorganic acid e.g. hydrochloric acid, sulfuric acid and the like or a strong organic acid such as p-toluenesulfonic acid is added to the reaction mixture. When R is hydrogen, only a catalytic amount of an acid is needed. If desired, the solvent can be held at the elevated temperature until all of the materials have gone into solution. After the solution has been held at the elevated temperature for the desired length of time, it is slowly cooled to ambient temperature. During the cooling process, the solution is preferably seeded with a condensation product of d-2-(6-methoxy-2-naphthyl)propanal with the resolving agent [e.g., the condensation product of d-2-(6-methoxy-2-naphthyl)propanal with a salt of N-n-propyl-D-glucamine]. The crystalline precipitate which results is enriched in the condensation product of d-2-(6-methoxy-2-naphthyl)propanal with the resolving agent. The final temperature to which the solution is taken is chosen by practical considerations but generally is selected so that the temperature difference will be sufficient to provide a high yield of crystals. The crystallizing mixture can be maintained at the lower temperature until crystallization is complete, or nearly so, usually for about 30 minutes to about several hours or so. The crystalline precipitate which results is removed by filtration and washed.

Prior to hydrolyzing the condensation product of d-2-(6-methoxy-2-naphthyl)propanal with the resolving agent, it is generally desirable to redissolve the enriched condensation product material in further solvent material, heating the solvent to the desired temperature, followed by seeding of the resultant solution with the condensation product of d-2-(6-methoxy-2-naphthyl)propanal with the resolving agent, and cooling to effect one or more further recrystallizations. Each such recrystallization further increases the proportion of the condensation product of d-2-(6-methoxy-2-napthyl)propanal with the resolving agent in the recrystallized material.

The condensation product of d-2-(6-methoxy-2-naphthyl)propanal with the resolving agent may be cleaved by any method which does not racemize the aldehyde such as by aqueous hydrolysis. The above aqueous solution is extracted with an organic solvent such as methylene dichloride. The solvent is evaporated and the crystalline aldehyde is recovered.

The d-2-(6-methoxy-2-naphthyl)propanal may be oxidized to d-2-(6-methoxy-2-naphthyl)propionic acid by any method which does not racemize the resultant acid. A suitable method, for example, is the method disclosed in French Pat. No. 2,377,370. The aldehyde and sulfamic acid in a solvent such as water in an inert solvent such as benzene are stirred with cooling. A sodium hypochlorite solution is added dropwise and the acid formed is recovered by conventional means such as filtration.

The material enriched in 1-2-(6-methoxy-2-naphthyl)propanal or the N-R-D-glucamine condensation product thereof (where R is as defined above) can be processed to recover 1-2-(6-methoxy-2-naphthyl)propanal which can then be racemized according to known techniques for racemizing aldehydes to give a material having a higher content of d-2-(6-methoxy-2-naphthyl)propanal such as under mild acidic or basis conditions. This material can be recycled, either alone or in combination with other d, 1-2-(6-methoxy-2-naphthyl)propanal, to provide additional starting material for the resolution process of this invention.

Those solutions containing the resolving agent as salts can be treated with an inorganic base forming an insoluble salt with the acid portion the N-R-D-glucamine salt, freeing the N-R-D-glucamine such as, for example, treatment with a suspension of calcium hydroxide to precipitate the corresponding calcium salt, e.g. calcium chloride, which is removed by filtration. The filtrate is concentrated under vacuum at elevated temperatures to dryness, first removing any further salt, e.g. the calcium salt, which is formed during the early stages of the concentration process. The residue is dissolved in a suitable solvent at an elevated temperature up to the reflux temperature of the solvent, and then cooled to room temperature, to thereby afford the resolving agent as a crystalline precipitate which can be reused, either alone or in combination with new material, in the resolution process of this invention. Alternatively, the resolving agent can be recovered through use of an anion exchange resin and recycled for reuse.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

EXAMPLE 1

4.30 G. of d,1-2-(6-methoxy-2-naphthyl)propanal is heated in 35 ml. of toluene to about the reflux temperature of the solvent to dissolve the d,1-2-(6-methoxy-2-naphthyl)propanal. 4.62 G of the HCl salt of N-methyl-D-glucamine is added and heating is continued. The solution is then cooled to room temperature (i.e. about 20°-23° C.) to give 4.46 g. of a material enriched in the condensation product of d-2-(6-methoxy-2-naphthyl)propanal with the hydrochloride salt of N-methyl-D-glucamine. A sample of the condensation product is hydrolyzed by dissolving in about 25 ml. of water at room temperature. The filtrate is extracted twice with methylene dichloride and the extracts are evaporated to give a material enriched in d-2-(6-methoxy-2-naphthyl)propanal. ($[\alpha]_D + 150°$ (dioxan)).

1.0 G d-2-(6-methoxy-2-naphthyl)propanal from the above step, 0.6 g sulfamic acid in 5 ml water and 7 ml benzene are stirred and cooled. 1 Ml of 24% sodium hypochlorite solution is added dropwise. The mixture is stirred and the organic phase is extracted with aqueous sodium bicarbonate. The extract is acidified to pH1. The solid which precipitates is collected and dried to give 0.75 g of d-2-(6-methoxy-2-naphthyl)propionic acid, m.p. 152°-153° C., $[\alpha]_D = +66°(c=1; CHCl_3)$.

EXAMPLE 2

4.30 G. of d,1-2-(6-methoxy-2-naphthyl)propanal is heated in 18 ml. of toluene to about the reflux temperature of the solvent to dissolve the d,1-2-(6-methoxy-2-naphthyl)propanal. 5.4 G. of the HCl salt of N-n-butyl-D-glucamine, is added and heating is continued. The solution is then cooled to room temperature to give 4.85 g. of a material enriched in the condensation product of d-2-(6-methoxy-2-naphthyl)-propanal with the hydrochloride salt of N-n-butyl-D-glucamine. 1.0 G. of the latter is hydrolyzed by dissolving in about 25 ml. of water at room temperature. The filtrate is extracted twice with methylene dichloride and the extracts are evaporated to give a material enriched in d-2-(6-methoxy-2-naphthyl)propanal. ($[\alpha]_D + 150°$ (dioxan)).

1.0 G d-2-(6-methoxy-2-naphthyl)propanal from the above step, 0.6 g sulfamic acid in 5 ml water and 7 ml benzene are stirred and cooled. 1 Ml of 24% sodium hypochlorite solution is added dropwise. The mixture is stirred and the organic phase is extracted with aqueous sodium bicarbonate. The extract is acidified to pH1. The solid which precipitates is collected and dried to give 0.75 g of d-2-(6-methoxy-2-naphthyl)propionic acid, m.p. 152°-153° C., $[\alpha]_D = +66°(c=1; CHCl_3)$.

EXAMPLE 3

4.30 G. of d,1 2-(6-methoxy-2-naphthyl)propanal is heated in 15 ml. of benzene to about the reflux temperature of the solvent to dissolve the d,1-2-(6-methoxy-2-naphthyl)propanal. 6.0 G. of the HCl salt of N-cyclohexyl-D-glucamine is added to the heated solution. The mixture is heated to about the reflux temperature of the solvent. The solution is cooled to room temperature to give 5.15 g. of a material enriched in the condensation product of d-2-(6-methoxy-2-naphthyl)propanal with the hydrochloride salt of N-cyclohexyl-D-glucamine. A sample of the latter is hydrolyzed by dissolving in about 25 ml. of water at room temperature. The filtrate is extracted twice with methylene dichloride and the extracts are evaporated to give a material enriched in d-2-(6-methoxy-2-naphthyl)propanal. ([α]$_D$+150° (dioxan)).

1.0 G d-2-(6-methoxy-2-naphthyl)propanal from the above step, 0.6 g sulfamic acid in 5 ml water and 7 ml benzene are stirred and cooled. 1 Ml of 24% sodium hypochlorite solution is added dropwise. The mixture is stirred and the organic phase is extracted with aqueous sodium bicarbonate. The extract is acidified to pH1. The solid which precipitates is collected and dried to give 0.75 g of d-2-(6-methoxy-2-naphthyl)propionic acid, m.p. 152°-153° C., [α]$_D$=+66°(c=1; CHCl$_3$).

EXAMPLE 4

4.30 G. of d,1-2-(6-methoxy-2-naphthyl)propanal is heated in 30 ml. of isopropanol to about the reflux temperature of the solvent to dissolve the d,1 2-(6-methoxy-2-naphthyl)propanal. 6.56 G. of the HCl salt of N-n-octyl-D-glucamine is added and heating is continued. The solution is cooled to room temperature to give 5.83 g. of a material enriched in the condensation product of d-2-(6-methoxy-2-naphthyl)-propanal with the hydrochloride salt of N-n-octyl-D-glucamine. A sample of the latter is hydrolyzed by dissolving in about 25 ml. of water at room temperature. The filtrate is extracted twice with methylene dichloride and the extracts are evaporated to give a material enriched in d-2-(6-methoxy-2-naphthyl)propanal. ([α]$_D$+150° (dioxan)).

1.0 G d-2-(6-methoxy-2-naphthyl)propanal from the above step, 0.6 g sulfamic acid in 5 ml water and 7 ml benzene are stirred and cooled. 1 Ml of 24% sodium hypochlorite solution is added dropwise. The mixture is stirred and the organic phase is extracted with aqueous sodium bicarbonate. The extract is acidified to pH1. The solid which precipitates is collected and dried to give 0.75 g of d-2-(6-methoxy-2-naphthyl)propionic acid, m.p. 152°-153° C., [α]$_D$=+66°(c=1; CHCl$_3$).

EXAMPLE 5

4.30 G. of d,1-2-(6-methoxy-2-naphthyl)propanal is heated in 15 ml. of toluene to about the reflux temperature of the solvent to dissolve the d,1-2-(6-methoxy-2-naphthyl)propanal. 7.82 G. of the HCl salt of N-n-dodecyl-D-glucamine is added and heating is continued. The solution is then cooled to room temperature to give 6.06 g. of a material enriched in the condensation product of d-2-(6-methoxy-2-naphthyl)propanal with the hydrochloride salt of N-n-dodecyl-D-glucamine. A sample of the latter is hydrolyzed by suspending in about 25 ml. of water at room temperature and holding at that temperature for 60 minutes, cooling and filtering. The filtrate is extracted twice with methylene dichloride and the extracts are evaporated to give a material enriched in d-2-(6-methoxy-2-naphthyl)propanal. ([α]$_D$+150° (dioxan)).

1.0 G d-2-(6-methoxy-2-naphthyl)propanal from the above step, 0.6 g sulfamic acid in 5 ml water and 7 ml benzene are stirred and cooled. 1 Ml of 24% sodium hypochlorite solution is added dropwise. The mixture is stirred and the organic phase is extracted with aqueous sodium bicarbonate. The extract is acidified to pH1. The solid which precipitates is collected and dried to give 0.75 g of d-2-(6-methoxy-2-naphthyl)propionic acid, m.p. 152°-153° C., [α]$_D$=+66°(c=1; CHCl$_3$).

EXAMPLE 6

4.30 G. of d,1-2-(6-methoxy-2-naphthyl)propanal in 10 ml. of isopropanol to about the reflux temperature of the solvent to dissolve the d,1-2-(6-methoxy-2-naphthyl)propanal. 9.4 G. of the HCl salt of N-n-octadecyl-D-glucamine is added, and the solution filtered while hot to remove some turbidity, cooled slightly, then seeded with a small amount of the condensation product of d-2-(6-methoxy-2-naphthyl)propanal with the hydrochloride salt of N-n-octadecyl-D-glucamine, and then cooled to room temperature to give 6.85 g. of a material enriched in the condensation product of d-2-(6-methoxy-2-naphthyl)propanal with the hydrochloride salt of N-n-octadecyl-D-glucamine. A sample of the latter is hydrolyzed by suspending in about 25 ml. of water at room temperature and holding at that temperature for 60 minutes, cooling and filtering. The filtrate is extracted twice with methylene dichloride and the extracts are evaporated to give a material enriched in d-2-(6-methoxy-2-naphthyl)propanal. ([α]$_D$+150° (dioxan)).

1.0 G d-2-(6-methoxy-2-naphthyl)propanal from the above step, 0.6 g sulfamic acid in 5 ml water and 7 ml benzene are stirred and cooled. 1 Ml of 24% sodium hypochlorite solution is added dropwise. The mixture is stirred and the organic phase is extracted with aqueous sodium bicarbonate. The extract is acidified to pH1. The solid which precipitates is collected and dried to give 0.75 g of d-2-(6-methoxy-2-naphthyl)propionic acid, m.p. 152°-153° C., [α]$_D$=+66°(c=1; CHCl$_3$).

What is claimed is:

1. A process for isolating a condensation product of d-2-(6-methoxy-2-naphthyl)propanal comprising
   crystallizing the condensation product of d-2-(6-methoxy-2-naphthyl)propanal with N-R-D-glucamine or a salt thereof wherein R is hydrogen, alkyl of 1 to 36 carbon atoms or cycloalkyl of 3 to 8 carbon atoms from a mixture containing a first condensation product of d-2-(6-methoxy-2-naphthyl)propanal with N-R-D-glucamine or a salt thereof and a second condensation product of 1-2-(6-methoxy-2-naphthyl)propanal with N-R-D-glucamine or a salt thereof in an inert solvent, the first condensation product being significantly less soluble in the inert solvent than the second condensation product at the crystallization temperature of the first condensation product.

2. A process for preparing a condensation product of d-2-(6-methoxy-2-naphthyl)propanal comprising
   reacting a racemic mixture of d,1-2-(6-methoxy-2-naphthyl)propanal with N-R-D-glucamine or a salt thereof wherein R is hydrogen, alkyl of 1 to 36 carbon atoms or cycloalkyl of 3 to 8 carbon atoms in an inert solvent to form a mixture of a first condensation product of d-2-(6-methoxy-2-naphthyl)-propanal with N-R-D-glucamine or a salt thereof and a second condensation product of 1-2-(6-methoxy-2-naphthyl)propanal with N-R-D-glucamine or a salt thereof, the first condensation product being significantly less soluble in the inert solvent than the second condensation product at the crystallization temperature of the first condensation product; and
   crystallizing the first condensation product from the mixture to yield a product enriched in the first condensation product.

3. A process for preparing d-2-(6-methoxy-2-naphthyl)propionic acid comprising
   crystallizing the condensation product of d-2-(6-methoxy-2-naphthyl)propanal with N-R-D-glucamine or a salt thereof wherein R is hydrogen, alkyl of 1 to 36 carbon atoms or cycloalkyl of 3 to 8 carbon atoms from a mixture containing a first condensation product of d-2-(6-methoxy-2-naphthyl)propanal with N-R-D-glucamine or a salt thereof and a second condensation product of 1-2-(6-methoxy-2-naphthyl)propanal with N-R-D-glucamine or a salt thereof in an inert solvent, the first condensation product being significantly less soluble in the inert solvent than the second condensation product at the crystallization temperature of the first condensation product;

hydrolyzing the first condensation product to obtain d-2-(6-methoxy-2-naphthyl)propanal; and oxidizing d-2-(6-methoxy-2-naphthyl)propanal to obtain d-2-(6-methoxy-2-naphthyl)propionic acid.

4. A process for preparing d-2-(6-methoxy-2-naphthyl)propionic acid comprising reacting a racemic mixture of d,1-2-(6-methoxy-2-naphthyl)propanal with N-R-D-glucamine or a salt thereof wherein R is hydrogen, alkyl of 1 to 36 carbon atoms or cycloalkyl of 3 to 8 carbon atoms in an inert solvent to form a mixture of a first condensation product of d-2-(6-methoxy-2-naphthyl)propanal with N-R-D-glucamine or a salt thereof and a second condensation product of 1-2-(6-methoxy-2-naphthyl)propanal with N-R-D-glucamine or a salt thereof, the first condensation product being significantly less soluble in the inert solvent than the second condensation product at the crystallization temperature of the first condensation product;

crystallizing the first condensation product from the mixture to yield a product enriched in the first condensation product;

hydrolyzing the first condensation product to obtain d-2-(6-methoxy-2-naphthyl)propanal; and oxidizing d-2-(6-methoxy-2-naphthyl)propanal to obtain d-2-(6-methoxy-2-naphthyl)propionic acid.

5. A process for preparing d-2-(6-methoxy-2-naphthyl)propionic acid comprising hydrolyzing a condensation product of d-2-(6-methoxy-2-naphthyl)propanal with N-R-D-glucamine or a salt thereof wherein R is hydrogen, alkyl of 1 to 36 carbon atoms or cycloalkyl of 3 to 8 carbon atoms to obtain d-2-(6-methoxy-2-naphthyl)propanal; and oxidizing d-2-(6-methoxy-2-naphthyl)propanal to obtain d-2-(6-methoxy-2-naphthyl)propionic acid.

6. The process of claim 1, 2, 3 or 4 including heating the mixture containing the condensation products in the inert solvent to solubilize the condensation products and cooling the heated mixture to subject the mixture to fractional crystallization to obtain a product enriched in the first condensation product.

7. The process of claim 1, 2, 3 or 4 including dissolving the first condensation product in an inert solvent and crystallizing the first condensation product substantially pure therefrom.

8. The process of claim 1, 2, 3 or 4 wherein the salt of N-R-D-glucamine is preformed.

9. The process of claim 1, 2, 3 or 4 wherein the salt of N-R-D-glucamine is formed in situ.

10. The process of claim 1, 2, 3, 4 or 5 wherein R is alkyl of 1 to 18 carbon atoms.

11. The process of claim 1, 2, 3, 4 or 5 wherein R is methyl, n-propyl, n-butyl or n-octyl.

12. The process of claim 1, 2, 3, 4 or 5 wherein R is cycloalkyl of 3 to 8 carbon atoms.

13. The process of claim 1, 2, 3, 4 or 5 wherein R is cyclohexyl.

14. The process of claim 1, 2, 3, 4 or 5 further including recovering a non-racemic mixture of d,1-2-(6-methoxy-2-naphthyl)propanal which remains after removal of the first condensation product from the mixture, racemizing the non-racemic mixture, and recycling the racemized mixture.

15. A mixture of the condensation product of d,1-2-(6-methoxy-2-naphthyl)propanal with N-R-D-glucamine or a salt thereof, wherein R is hydrogen, alkyl of 1 to 36 carbon atoms or cycloalkyl of 3 to 8 carbon atoms.

16. The condensation products of claim 15, wherein R is alkyl of 1 to 18 carbon atoms or cyclohexyl.

17. A resolving medium comprising a mixture of a first condensation product of d-2-(6-methoxy-2-naphthyl)propanal with N-R-D-glucamine or a salt thereof and a second condensation product of 1-2-(6-methoxy-2-naphthyl)propanal with N-R-D-glucamine or a salt thereof wherein R is hydrogen, alkyl of 1 to 36 carbon atoms or cycloalkyl of 3 to 8 carbon atoms, and a solvent in which the first condensation product is less soluble than the second condensation product to permit fractional crystallization of said condensation products upon the cooling of said medium from an elevated temperature.

* * * * *